United States Patent
Slaga et al.

(10) Patent No.: US 12,410,209 B2
(45) Date of Patent: Sep. 9, 2025

(54) MODIFIED GLUCOCORTICOIDS

(71) Applicant: Board of Regents, The University of Texas System, Austin, TX (US)

(72) Inventors: Thomas J. Slaga, San Antonio, TX (US); Daniel Glade, San Antonio, TX (US); Anna Mancha Ramirez, San Antonio, TX (US); Huiyun Liang, San Antonio, TX (US); Rita Ghosh, San Antonio, TX (US)

(73) Assignee: Board of Regents, The University of Texas System, Austin, TX (US)

( * ) Notice: Subject to any disclaimer, the term of this patent is extended or adjusted under 35 U.S.C. 154(b) by 0 days.

(21) Appl. No.: 17/362,440

(22) Filed: Jun. 29, 2021

(65) Prior Publication Data

US 2022/0411460 A1      Dec. 29, 2022

(51) Int. Cl.
*C07J 7/00* (2006.01)

(52) U.S. Cl.
CPC ..................... *C07J 7/009* (2013.01)

(58) Field of Classification Search
CPC ....................................... C07J 7/009
See application file for complete search history.

(56) References Cited

U.S. PATENT DOCUMENTS

| | | |
|---|---|---|
| 3,723,484 A | 3/1973 | Laurent et al. |
| 3,971,773 A | 7/1976 | Cimarusti et al. |
| 4,588,718 A | 5/1986 | Anderson et al. |
| 5,356,633 A | 10/1994 | Woodle et al. |
| 7,361,645 B2 | 4/2008 | Bohlmann et al. |

FOREIGN PATENT DOCUMENTS

| | | |
|---|---|---|
| WO | WO 2011/109711 A1 | 9/2011 |
| WO | WO 2015/010054 A2 | 1/2015 |

OTHER PUBLICATIONS

Nixon et al. (Journal of Endocrinology, 2012, 212, 111-127).*
Silverman (The Organic Chemistry of Drug Design and Drug Action, Academic Press. Inc. 1992, 19-23).*
Choe et al. (Journal of Medicinal Chemistry, 1995, 38(5), 816-825).*
Hsing et al. PLoS One 2011, 6(3):e17598.
Chen et al. Mol Cell Biol 2005, 25(18):7966-7975.
Chen et al. EMBO J 2002, 21(23):6539-6548.
Kiernan et al. J Biol Chem 2003, 278(4):2758-2766.
Kundu and Surh. Mutat Res 2008, 659(1-2):15-30.
Ibiebele et al. Am J Clin Nutr 2007, 85(5):1401-1408.
Kune et al. Nutr Cancer 1992, 18(3):237-244.
Aziz et al. FASEB J 2005, 19(9):1193-1195.
Kapadia et al. Pharmacol Res 2002, 45(6):499-505.
Huang et al. Cancer Res 1994, 54(3):701-708.
Tokuda et al. Cancer Lett 1986, 33(3):279-285.
Xia and Weng. J Diabetes 2010, 2(4):243-249.
Graf et al. Curr Opin Investig Drugs 2010, 11(10):1107-1115.
Cherniack. Nutrition 2011, 27(6):617-623.
Leiherer et al. Vascul Pharmacol 2013, 58(1-2):3-20.
Hattori et al. Hypertension 2006, 47(6):1183-1188.
Musi et al. Diabetes 2002, 51(7):2074-2081.
Zhou et al. J Clin Invest 2001, 108(8):1167-1174.
Hardie et al. Chem Biol 2012, 19(10):1222-1236.
Baur et al. Nature 2006, 444(7117):337-342.
Brasnyo et al. Br J Nutr 2011, 106(3):383-389.
Jang et al. Int Immunopharmacol 2009, 9(1):113-119.
Somova et al. Phytomedicine 2003, 10(2-3):115-121.
Timmers et al. Cell Metab 2011, 14(5):612-622.
Xu and Si. Nutr Res 2012,32(9):648-658.
Um et al. Diabetes 2010, 59(3):554-563.
Zheng et al. Biochem Biophys Res Commun 2012, 419(4):741-747.
Huang et al. Biochem J 2008, 412(2):211-221.
Faubert et al. Cell Metab 2013, 17(1):113-124.
Kimura et al. Food Chem Toxicol 2010, 48(1):429-435.
Taesotikul et al. Drug Metab Pharmacokinet 2011, 26(2):154-161.
Lu et al. J Nutr Biochem 2005, 16(1):23-30.
Suganuma et al. Cancer Res 1999, 59(1):44-47.
Khafif et al. Carcinogenesis 1998, 19(3):419-424.
Saw et al. Biopharm Drug Dispos 2011, 32(5):289-300.
Al-Abd et al. Cell Prolif 2011;44(6):591-601.
Quan et al. Biomed Pharmacother 2008;62(9):622-629.
Shan et al. Chin J Integr Med 2011, 17(8):607-611.
Zhang et al. Int J Biochem Cell Biol 2012, 44(8):1244-1253.
Shi et al. Eur J Pharmacol 2011;669(1-3):38-44.
Hardy et al., Therapeutic glucocorticoids: mechanisms of actions in rheumatic diseases. Nat Rev Rheumatology. 16, 133-144 (2020).
Lillegraven, S. et al. Immunosuppressive treatment and the risk of diabetes in rheumatoid arthritis. PLoS One 14, e0210459 (2019).
Overman, R. A., Yeh, J. Y. & Deal, C. L. Prevalence of oral glucocorticoid usage in the United States: a general population perspective. Arthritis Care Res. 65, 294-298 (2013).

* cited by examiner

*Primary Examiner* — Susanna Moore

(57) ABSTRACT

Certain embodiments are directed to modified glucocorticoid compounds having one or both of (i) a substitution of a halogen for the 11 hydroxy and/or (ii) reduction of the bond between carbon 4 and carbon 5 of the A ring.

2 Claims, 3 Drawing Sheets

MODIFIED GLUCOCORTICOIDS

STATEMENT REGARDING FEDERALLY FUNDED RESEARCH

None.

BACKGROUND

Inflammation normally is a localized, protective response to trauma or microbial invasion that destroys, dilutes, or walls-off the injurious agent and the injured tissue. Diseases characterized by inflammation are significant causes of morbidity and mortality in humans. While inflammation commonly occurs as a defensive response to invasion of the host by foreign material, it is also triggered by a response to mechanical trauma, toxins, and neoplasia. Excessive inflammation caused by abnormal recognition of host tissue as foreign, or prolongation of the inflammatory process, may lead to inflammatory diseases such as diabetes, asthma, atherosclerosis, cataracts, reperfusion injury, cancer, post-infectious syndromes such as in infectious meningitis, and rheumatic fever and rheumatic diseases such as systemic lupus erythematosus and rheumatoid arthritis. Thus, there is a need to produce agents that inhibit inflammation in many such diseases.

Glucocorticoids are used therapeutically as replacement therapy for individuals having adrenal insufficiencies, due to pathologies in the hypothalamus, anterior pituitary or the adrenal cortex. The glucocorticoids are also used for the treatment of a diverse number of non-endocrine diseases. Except in patients receiving replacement or substitution therapy, glucocorticoids are neither specific nor curative: they provide symptomatic relief by virtue of their anti-inflammatory and immunosuppressive properties. Glucocorticoids are used to treat rheumatic disorders such as rheumatoid arthritis, systemic lupus erythematosus, and a variety of vasculitic disorders such as polyarteritis nodosa, Wegener's granulomatosis and giant cell arteritis. In non-inflammatory degenerative joint diseases (e.g., osteoarthritis) or in a variety of regional pain syndromes (e.g., tendonitis or bursitis), glucocorticoids may be administered by local injection for the treatment of episodic disease flare-up.

However, as useful as glucocorticoids are, they do have severe side-effects. Two categories of toxic effects result from the therapeutic use of glucocorticoids: those resulting from withdrawal of glucocorticoid therapy and those resulting from continued use of supraphysiological doses. The most severe complication of the termination of glucocorticoid treatment is acute adrenal insufficiency, which results from too rapid a withdrawal of glucocorticoids after prolonged therapy, in which the hypothalamus/pituitary/adrenal (HPA) axis has been suppressed. Besides the consequences that result from the suppression of the HPA system, there are a number of other complications that result from prolonged glucocorticoid therapy, including fluid and electrolyte abnormalities, hypertension, hyperglycemia, increased susceptibility to infection, cataracts, growth arrest, fat redistribution, striae, ecchymosis, acne, hirsutism, and thymic atrophy.

There remains a need for glucocorticoid molecules having attenuated deleterious side-effects.

SUMMARY

To address the deleterious side-effects of glucocorticoids the inventors modified glucocorticoid compounds by (i) substitution of a halogen for the 11 hydroxy and/or (ii) reduction of the A ring, as shown with a representative molecule cortisol. First, the hydroxyl group was removed at the eleventh carbon position to circumvent the upregulation of 11βHSD2 and was replaced with a halogen, e.g., fluorine. Second, two hydrogens were added to saturate the double bond between carbons four and five of the A ring, a 5-α-reduction, which is the location on cortisol that induces gluconeogenesis. Similar modifications can be made in dexamethasone, triamcinolone, fluocinolone acetonide, budesonide, prednisone, and other glucocorticoid compounds.

Certain embodiments are directed to modified glucocorticoids including compounds having a structure of Formula I or Formula II.

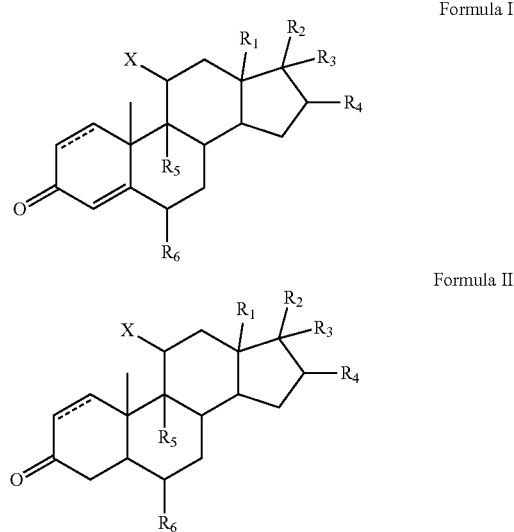

Formula I

Formula II

Certain embodiments are directed to a compound of Formula I or Formula II where:

The bond between carbons one and two is saturated or is a double bond.

$R_1$ is selected from hydrogen, hydroxyl, C1 to C3 alkyl, C1 to C3 alcohol, ester, substituted ester, ether, substituted ether, C1 to C3 carboxylic acid, ketone, substituted ketone, C1 to C3 amide, or C1 to C3 aldehyde group. In certain aspects the substitution is an alkyl, alkoxy, hydroxyl, sulfhydryl, of amide.

$R_2$ is selected from hydrogen, hydroxyl, C1 to C3 alkyl, C1 to C3 alcohol, ester, substituted ester, ether, substituted ether, C1 to C3 carboxylic acid, C3 to C5 ketone, C3 to C5 substituted ketone, C1 to C3 amide, or C1 to C3 aldehyde group. In certain aspects the substitution is an alkyl, alkoxy, hydroxyl, sulfhydryl, of amide. In certain aspects, $R_2$ is a C3 to C5 hydroxy ketone (e.g., hydroxy acetone).

$R_3$ is selected from hydrogen, halogen, or hydroxyl.

$R_4$ is selected from hydrogen, halogen, or hydroxyl.

In certain aspects $R_3$ and $R_4$ form a 5 or 6 member cycloalkyl or heterocycle. In certain aspects the heterocycle is a 5 member nitrogen or oxygen heterocycle. In certain aspects $R_3$ and $R_4$ form a substituted or unsubstituted dioxolane. In certain aspects the substituted dioxolane is acetonide.

$R_5$ and $R_6$ are independently selected from hydrogen, hydroxide, fluorine, chlorine, bromine, or iodine.

X is a halogen. In certain embodiments X is fluorine or chlorine.

Certain embodiments are directed to methods and compositions for treating inflammation, obesity, diabetes, and/or cancer with a combination of a modified glucocorticoid as described herein in combination with ursolic acid, resveratrol, or ursolic acid and resveratrol.

Ursolic acid is a phytonutrient found in a wide variety of food products and herbs especially apples, olives, and rosemary. Ursolic acid inhibits chronic inflammation and increases the effectiveness of anti-diabetic drugs such as Rosiglitazone and Metformin on glucose uptake into insulin resistant fat cells.

Resveratrol is a phytonutrient found in the skin of red grapes and in other fruits. Resveratrol exerts many of its beneficial effects through its ability to mimic and enhance the effects of calorie restriction and exercise.

Certain embodiments are directed to methods comprising administering an effective amount of a modified glucocorticoid as described herein in combination with an effective amount of ursolic acid and an effective amount of resveratrol to a subject in need thereof. In certain aspects the modified steroid is administered first followed by ursolic acid/resveratrol combination. The modified steroid is used as would its parent compound with reduced side effects. The combination with ursolic acid and resveratrol further reduces or mitigates side effects. Glucocorticoids are a type of corticosteroid hormone that is very effective at reducing inflammation and suppressing the immune system. Inflammation is the way our immune system responds to harmful substances and trauma and is part of our healing process. However, if the usual control mechanisms that turn the process of inflammation off are not functioning properly and it continues unabated, our tissues can become damaged. Glucocorticoids can be used to ameliorate inflammation.

Glucocorticoids may be used in low doses in adrenal insufficiency. In much higher doses, oral or inhaled glucocorticoids are used to suppress various allergic, inflammatory, and autoimmune disorders. Inhaled glucocorticoids are the second-line treatment for asthma. They are also administered as post-transplantory immunosuppressants to prevent the acute transplant rejection and the graft-versus-host disease. Glucocorticoids can be used in the treatment of heart failure to increase the renal responsiveness to diuretics and natriuretic peptides. Glucocorticoids are historically used for pain relief in inflammatory conditions.

Any glucocorticoid can be given in a dose that provides approximately the same glucocorticoid effects as normal cortisol production; this is referred to as physiologic, replacement, or maintenance dosing. This is approximately 6 to 12 mg/m$^2$/day of hydrocortisone (m$^2$ refers to body surface area (BSA), and is a measure of body size; an average man's BSA is 1.9 m$^2$).

Glucocorticoids cause immunosuppression, and the therapeutic component of this effect is mainly the decreases in the function and numbers of lymphocytes, including both B cells and T cells. The major mechanism for this immunosuppression is through inhibition of nuclear factor kappa-light-chain-enhancer of activated B cells (NF-κB). NF-κB is a critical transcription factor involved in the synthesis of many mediators (i.e., cytokines) and proteins (i.e., adhesion proteins) that promote the immune response. Inhibition of this transcription factor, therefore, blunts the capacity of the immune system to mount a response. Glucocorticoids suppress cell-mediated immunity by inhibiting genes that code for the cytokines IL-1, IL-2, IL-3, IL-4, IL-5, IL-6, IL-8 and IFN-y, the most important of which is IL-2. Smaller cytokine production reduces the T cell proliferation.

Glucocorticoids also suppress the humoral immunity, thereby causing a humoral immune deficiency. Glucocorticoids cause B cells to express smaller amounts of IL-2 and of IL-2 receptors. This diminishes both B cell clone expansion and antibody synthesis. The diminished amounts of IL-2 also cause fewer T lymphocyte cells to be activated.

Glucocorticoids are potent anti-inflammatories, regardless of the inflammation's cause; their primary anti-inflammatory mechanism is lipocortin-1 (annexin-1) synthesis. Lipocortin-1 both suppresses phospholipase A2, thereby blocking eicosanoid production, and inhibits various leukocyte inflammatory events (epithelial adhesion, emigration, chemotaxis, phagocytosis, respiratory burst, etc.). In other words, glucocorticoids not only suppress immune response, but also inhibit the two main products of inflammation, prostaglandins and leukotrienes. They inhibit prostaglandin synthesis at the level of phospholipase A2 as well as at the level of cyclooxygenase/PGE isomerase (COX-1 and COX-2), the latter effect being much like that of NSAIDs, thus potentiating the anti-inflammatory effect.

Glucocorticoids marketed as anti-inflammatories are often topical formulations, such as nasal sprays for rhinitis or inhalers for asthma. These preparations have the advantage of only affecting the targeted area, thereby reducing side effects or potential interactions. In this case, the main compounds used are beclometasone, budesonide, fluticasone, mometasone and ciclesonide. In rhinitis, sprays are used. For asthma, glucocorticoids are administered as inhalants with a metered-dose or dry powder inhaler. In rare cases, symptoms of radiation induced thyroiditis has been treated with oral glucocorticoids.

Glucocorticoids can be used in the management of familial hyperaldosteronism type 1. They are not effective, however, for use in the type 2 condition.

A modified glucocorticoid as described herein is administered at a dose of between 10, 20, 30, 40, 50, 100, 150, 200, 250, 300 to 250, 300, 350, 400, 450, 500, 550, 600 mg/day, including all values and ranges there between. In certain aspects 10, 20, 30, 40, 50, 100, 150, 200, 250, 300, 350, 400, 450, 500, 550, or 600 mg of a modified glucocorticoid is administered. In a further aspect the dose of modified glucocorticoid is administered in one dose or in multiple doses over 0.5, 1, 2, 3, 4, 5, 6, 7, 8, 9, or 10 minutes, hours or days.

An ursolic acid is administered at a dose of between 50, 100, 150, 200, 250, 300 to 250, 300, 350, 400, 450, 500, 550, 600 mg/day, including all values and ranges there between. In certain aspects 50, 100, 150, 200, 250, 300, 350, 400, 450, 500, 550, or 600 mg of ursolic acid is administered. In a further aspect the dose of ursolic acid is administered in one dose or in multiple doses over 0.5, 1, 2, 3, 4, 5, 6, 7, 8, 9, or 10 minutes, hours or days.

A resveratrol is administered at a dose of between 50, 100, 150, 200, 250, 300 to 250, 300, 350, 400, 450, 500, 550, 600 mg/day, including all values and ranges there between. In certain aspects 50, 100, 150, 200, 250, 300, 350, 400, 450, 500, 550, or 600 mg of resveratrol is administered. In a further aspect the dose of resveratrol is administered in one dose or in multiple doses over 0.5, 1, 2, 3, 4, 5, 6, 7, 8, 9, or 10 minutes, hours or days.

In certain aspects ursolic acid and resveratrol are administered at a ratio of 4:1, 3:1, 2:1, 1:1, 1:2, 1:3, or 1:4, including all values and ranges there between. In certain aspects modified glucocorticoid, ursolic acid, and resveratrol are administered individually. Individual administration refers to the compounds being formulated is separate formulations. The compounds when administered individually can be administered at the same time or within about 1, 2, 3, 4, 5, 6, 7, 8, 9, or 10 minutes, hours, or days. In certain aspects two or three of modified glucocorticoid, ursolic acid, and/or resveratrol are formulated in the same composition. Two or all three of the components can be formulated as a tablet, a capsule, a concentrate, a powder, a beverage, a baked good, chocolate, caramel, cookie, bar, and/or snack. In certain aspects one or more of modified glucocorticoid, ursolic acid, and/or resveratrol are administered orally.

Certain embodiments are directed to compositions and methods for treating certain cancers or skin cancer comprising administering an effective amount of modified glucocorticoid or an effective amount of modified glucocorticoid in combination with an effective amount of ursolic acid and resveratrol. A modified glucocorticoid as described herein is administered at a dose of between 10, 20, 30, 40, 50, 100, 150, 200, 250, 300 to 250, 300, 350, 400, 450, 500, 550, 600 mg/day, including all values and ranges there between. In certain aspects 10, 20, 30, 40, 50, 100, 150, 200, 250, 300, 350, 400, 450, 500, 550, or 600 mg of a modified glucocorticoid is administered. In a further aspect the dose of modified glucocorticoid is administered in one dose or in multiple doses over 0.5, 1, 2, 3, 4, 5, 6, 7, 8, 9, or 10 minutes, hours or days. In certain aspects ursolic acid is administered at a dose of between 50, 100, 150, 200, 250, 300 to 250, 300, 350, 400, 450, 500, 550, 600 mg/day, including all values and ranges there between. In certain aspects 50, 100, 150, 200, 250, 300, 350, 400, 450, 500, 550, or 600 mg of ursolic acid is administered. In a further aspect the dose of ursolic acid is administered in one dose or in multiple doses over 0.5, 1, 2, 3, 4, 5, 6, 7, 8, 9, or 10 minutes, hours or days. In certain aspects resveratrol is administered at a dose of between 50, 100, 150, 200, 250, 300 to 250, 300, 350, 400, 450, 500, 550, 600 mg/day, including all values and ranges there between. In certain aspects 50, 100, 150, 200, 250, 300, 350, 400, 450, 500, 550, or 600 mg of resveratrol is administered. In a further aspect the dose of resveratrol is administered in one dose or in multiple doses over 0.5, 1, 2, 3, 4, 5, 6, 7, 8, 9, or 10 minutes, hours or days. In certain aspects ursolic acid and resveratrol are administered at a ratio of 4:1, 3:1, 2:1, 1:1, 1:2, 1:3, or 1:4, including all values and ranges there between. In certain aspects ursolic acid and resveratrol are administered individually. Individual administration refers to the compounds being formulated is separate formulations. The compounds when administered individually can be administered at the same time or within about 1, 2, 3, 4, 5, 6, 7, 8, 9, or 10 minutes, hours, or days. In certain aspects ursolic acid and resveratrol are formulated in the same composition. Ursolic acid and/or resveratrol can be formulated as a topical solution (crème, ointment, gel, etc.), tablet, a capsule, a concentrate, a powder, a beverage, a baked good, chocolate, caramel, cookie, bar, and/or snack. In certain aspects ursolic acid and/or resveratrol are administered topically. In certain aspects ursolic acid and/or resveratrol are administered orally.

Other embodiments of the invention are discussed throughout this application. Any embodiment discussed with respect to one aspect of the invention applies to other aspects of the invention as well and vice versa. Each embodiment described herein is understood to be embodiments of the invention that are applicable to all aspects of the invention. It is contemplated that any embodiment discussed herein can be implemented with respect to any method or composition of the invention, and vice versa. Furthermore, compositions and kits of the invention can be used to achieve methods of the invention.

The use of the word "a" or "an" when used in conjunction with the term "comprising" in the claims and/or the specification may mean "one," but it is also consistent with the meaning of "one or more," "at least one," and "one or more than one."

Throughout this application, the term "about" is used to indicate that a value includes the standard deviation of error for the device or method being employed to determine the value.

The use of the term "or" in the claims is used to mean "and/or" unless explicitly indicated to refer to alternatives only or the alternatives are mutually exclusive, although the disclosure supports a definition that refers to only alternatives and "and/or."

As used in this specification and claim(s), the words "comprising" (and any form of comprising, such as "comprise" and "comprises"), "having" (and any form of having, such as "have" and "has"), "including" (and any form of including, such as "includes" and "include") or "containing" (and any form of containing, such as "contains" and "contain") are inclusive or open-ended and do not exclude additional, unrecited elements or method steps.

As used herein, the terms "comprises," "comprising," "includes," "including," "has," "having," "contains", "containing," "characterized by" or any other variation thereof, are intended to encompass a non-exclusive inclusion, subject to any limitation explicitly indicated otherwise, of the recited components. For example, a chemical composition and/or method that "comprises" a list of elements (e.g., components or features or steps) is not necessarily limited to only those elements (or components or features or steps), but may include other elements (or components or features or steps) not expressly listed or inherent to the chemical composition and/or method.

As used herein, the transitional phrases "consists of" and "consisting of" exclude any element, step, or component not specified. For example, "consists of" or "consisting of" used in a claim would limit the claim to the components, materials or steps specifically recited in the claim except for impurities ordinarily associated therewith (i.e., impurities within a given component). When the phrase "consists of" or "consisting of" appears in a clause of the body of a claim, rather than immediately following the preamble, the phrase "consists of" or "consisting of" limits only the elements (or components or steps) set forth in that clause; other elements (or components) are not excluded from the claim as a whole.

As used herein, the transitional phrases "consists essentially of" and "consisting essentially of" are used to define a chemical composition and/or method that includes materials, steps, features, components, or elements, in addition to those literally disclosed, provided that these additional materials, steps, features, components, or elements do not materially affect the basic and novel characteristic(s) of the claimed invention. The term "consisting essentially of" occupies a middle ground between "comprising" and "consisting of".

Other objects, features and advantages of the present invention will become apparent from the following detailed description. It should be understood, however, that the detailed description and the specific examples, while indicating specific embodiments of the invention, are given by way of illustration only, since various changes and modifications within the spirit and scope of the invention will become apparent to those skilled in the art from this detailed description.

DESCRIPTION OF THE DRAWINGS

The following drawings form part of the present specification and are included to further demonstrate certain aspects of the present invention. The invention may be better understood by reference to one or more of these drawings in combination with the detailed description of the specification embodiments presented herein.

DESCRIPTION

Figure 1:
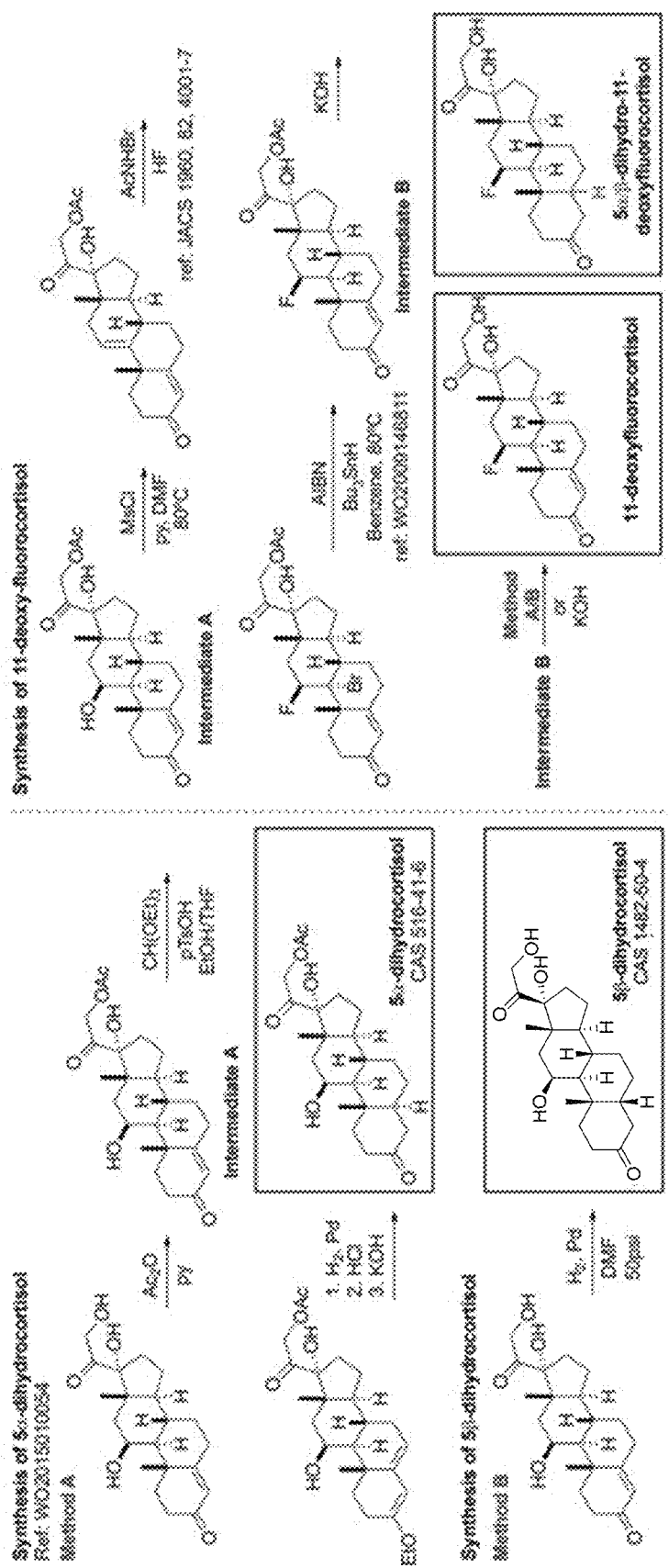
FIG. 1. Synthesis scheme for modified glucocorticoids.

The following discussion is directed to various embodiments of the invention. The term "invention" is not intended to refer to any particular embodiment or otherwise limit the scope of the disclosure. Although one or more of these embodiments may be preferred, the embodiments disclosed should not be interpreted, or otherwise used, as limiting the scope of the disclosure, including the claims. In addition, one skilled in the art will understand that the following description has broad application, and the discussion of any embodiment is meant only to be exemplary of that embodiment, and not intended to intimate that the scope of the disclosure, including the claims, is limited to that embodiment.

Glucocorticoids remain one of the major treatments for skin cancer and acute lymphoblastic leukemia. Glucocorticoids execute cytotoxic effect by binding to glucocorticoid receptor, which translocates to the nucleus, binds to glucocorticoid response elements, regulates transcription of target genes and eventually leads to induction of cell cycle arrest and apoptosis. GCs also transrepress NF-κB and AP1 signaling pathways to exert anti-inflammatory functions. Chronic inflammation plays important roles in tumor initiation and progression.

Two enzymes, 11β-hydroxysteroid dehydrogenase type 1 and type 2 (11β-HSD1 and 2) regulate the amount of active glucocorticoids available to glucocorticoid receptors in a tissue specific manner. 11β-HSD1 is responsible for activation by converting the ketone at the 11th carbon to a hydroxyl group and 11β-HSD2 does the opposite. Using an in vitro model the inventors found a significant amount of up-regulation of 11β-HSD2 protein expression in non-melanoma skin cancer cells versus normal counter parts.

Two modifications were made using cortisol as a representative glucocorticoid. First, the hydroxyl group was removed at the eleventh carbon position to circumvent the upregulation of 11β-HSD2 and was replaced with a halogen. Second, two hydrogens were added to saturate the double bond between carbons four and five, a 5-α-reduction, which is the location of cortisol that induces gluconeogenesis. Similar modifications can be done in dexamethasone, triamcinolone, fluocinolone acetonide, and other glucocorticoids. Potentially making modified glucocorticoids more effective at preventing myeloma, childhood leukemias, lung cancer, and skin cancer than the unmodified glucocorticoids.

I. Modified Glucocorticoids

Modified glucocorticoids include compounds having a structure of Formula I or Formula II.

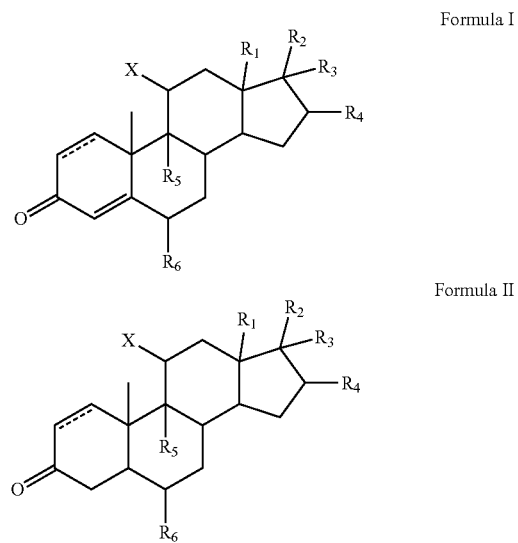

Certain embodiments are directed to a compound of Formula I or Formula II where the bond between carbons one and two is saturated or a double bond.

$R_1$ is selected from hydrogen, hydroxyl, C1 to C3 alkyl, C1 to C3 alcohol, ester, substituted ester, ether, substituted ether, C1 to C3 carboxylic acid, ketone, substituted ketone, C1 to C3 amide, or C1 to C3 aldehyde group. In certain aspects the substitution is an alkyl, alkoxy, hydroxyl, sulfhydryl, of amide.

$R_2$ is selected from hydrogen, hydroxyl, C1 to C3 alkyl, C1 to C3 alcohol, ester, substituted ester, ether, substituted ether, C1 to C3 carboxylic acid, C3 to C5 ketone, C3 to C5 substituted ketone, C1 to C3 amide, or C1 to C3 aldehyde group. In certain aspects the substitution is an alkyl, alkoxy, hydroxyl, sulfhydryl, of amide. In certain aspects, $R_2$ is a C3 to C5 hydroxy ketone (e.g., hydroxy acetone).

$R_3$ is selected from hydrogen, halogen, or hydroxyl.

$R_4$ is selected from hydrogen, halogen, or hydroxyl.

In certain aspects $R_3$ and $R_4$ form heterocycle. In certain aspects the heterocycle is a 5 member nitrogen or oxygen heterocycle. In certain aspects $R_3$ and $R_4$ form a substituted or unsubstituted dioxolane. The substituted dioxolane can acetonide.

$R_5$ and $R_6$ are independently selected from hydrogen, hydroxide, fluorine, chlorine, bromine, or iodine.

X is a halogen. In certain embodiments X is fluorine or chlorine.

As used herein, "predominantly one enantiomer" means that the compound contains at least 85% of one enantiomer, or more preferably at least 90% of one enantiomer, or even more preferably at least 95% of one enantiomer, or most preferably at least 99% of one enantiomer. Similarly, the phrase "substantially free from other optical isomers" means that the composition contains at most 5% of another enantiomer or diastereomer, more preferably 2% of another enantiomer or diastereomer, and most preferably 1% of another enantiomer or diastereomer.

As used herein, the term "water soluble" means that the compound dissolves in water at least to the extent of 0.010 mole/liter or is classified as soluble according to literature precedence.

As used herein, the term "nitro" means —$NO_2$; the term "halo" designates —F, —Cl, —Br or —I; the term "mercapto" means —SH; the term "cyano" means —CN; the term "azido" means —$N_3$; the term "silyl" means —$SiH_3$, and the term "hydroxy" means —OH.

The term "alkyl," by itself or as part of another substituent, means, unless otherwise stated, a linear (i.e., unbranched) or branched carbon chain, which may be fully saturated, mono- or polyunsaturated. An unsaturated alkyl group is one having one or more double bonds or triple bonds. Saturated alkyl groups include those having one or more carbon-carbon double bonds (alkenyl) and those having one or more carbon-carbon triple bonds (alkynyl). The groups, —$CH_3$ (Me), —$CH_2CH_3$ (Et), —$CH_2CH_2CH_3$ (n-Pr), —$CH(CH_3)_2$ (iso-Pr), —$CH_2CH_2CH_2CH_3$ (n-Bu), —$CH(CH_3)CH_2CH_3$ (sec-butyl), —$CH_2CH(CH_3)_2$ (isobutyl), —$C(CH_3)_3$ (tent-butyl), —$CH_2C(CH_3)_3$ (neo-pentyl), are all non-limiting examples of alkyl groups.

The term "heteroalkyl," by itself or in combination with another term, means, unless otherwise stated, a linear or branched chain having at least one carbon atom and at least one heteroatom selected from the group consisting of O, N, S, P, and Si. In certain embodiments, the heteroatoms are selected from the group consisting of O and N. The heteroatom(s) may be placed at any interior position of the heteroalkyl group or at the position at which the alkyl group is attached to the remainder of the molecule. Up to two heteroatoms may be consecutive. The following groups are all non-limiting examples of heteroalkyl groups: trifluoromethyl, —$CH_2F$, —$CH_2Cl$, —$CH_2Br$, —$CH_2OH$, —$CH_2OCH_3$, —$CH_2OCH_2CF_3$, —$CH_2OC(O)CH_3$, —$CH_2NH_2$, —$CH_2NHCH_3$, —$CH_2N(CH_3)_2$, —$CH_2CH_2Cl$, —$CH_2CH_2OH$, $CH_2CH_2OC(O)CH_3$, —$CH_2CH_2NHCO_2C(CH_3)_3$, and —$CH_2Si(CH_3)_3$.

The terms "cycloalkyl" and "heterocyclyl," by themselves or in combination with other terms, means cyclic versions of "alkyl" and "heteroalkyl", respectively. Additionally, for heterocyclyl, a heteroatom can occupy the position at which the heterocycle is attached to the remainder of the molecule.

The term "aryl" means a polyunsaturated, aromatic, hydrocarbon substituent. Aryl groups can be monocyclic or polycyclic (e.g., 2 to 3 rings that are fused together or linked covalently). The term "heteroaryl" refers to an aryl group that contains one to four heteroatoms selected from N, O, and S. A heteroaryl group can be attached to the remainder of the molecule through a carbon or heteroatom. Non-limiting examples of aryl and heteroaryl groups include phenyl, 1-naphthyl, 2-naphthyl, 4-biphenyl, 1-pyrrolyl, 2-pyrrolyl, 3-pyrrolyl, 3-pyrazolyl, 2-imidazolyl, 4-imidazolyl, pyrazinyl, 2-oxazolyl, 4-oxazolyl, 2-phenyl-4-oxazolyl, 5-oxazolyl, 3-isoxazolyl, 4-isoxazolyl, 5-isoxazolyl, 2-thiazolyl, 4-thiazolyl, 5-thiazolyl, 2-furyl, 3-furyl, 2-thienyl, 3-thienyl, 2-pyridyl, 3-pyridyl, 4-pyridyl, 2-pyrimidyl, 4-pyrimidyl, 5-benzothiazolyl, purinyl, 2-benzimidazolyl, 5-indolyl, 1-isoquinolyl, 5-isoquinolyl, 2-quinoxalinyl, 5-quinoxalinyl, 3-quinolyl, and 6-quinolyl. Substituents for each of the above noted aryl and heteroaryl ring systems are selected from the group of acceptable substituents described below.

Various groups are described herein as substituted or unsubstituted (i.e., optionally substituted). Optionally substituted groups may include one or more substituents independently selected from: halogen, nitro, cyano, hydroxy, amino, mercapto, formyl, carboxy, oxo, carbamoyl, substituted or unsubstituted alkyl, substituted or unsubstituted heteroalkyl, alkoxy, alkylthio, alkylamino, (alkyl)2amino, alkylsulfinyl, alkyl sulfonyl, aryl sulfonyl, substituted or unsubstituted cycloalkyl, substituted or unsubstituted heterocyclyl, substituted or unsubstituted aryl, and substituted or unsubstituted heteroaryl. In certain aspects the optional substituents may be further substituted with one or more substituents independently selected from: halogen, nitro, cyano, hydroxy, amino, mercapto, formyl, carboxy, carbamoyl, unsubstituted alkyl, unsubstituted heteroalkyl, alkoxy, alkylthio, alkylamino, (alkyl)$_2$amino, alkylsulfinyl, alkyl sulfonyl, aryl sulfonyl, unsubstituted cycloalkyl, unsubstituted heterocyclyl, unsubstituted aryl, or unsubstituted heteroaryl. Exemplary optional substituents include, but are not limited to: —OH, oxo (═O), —F, Br, $C_{1-4}$alkyl, phenyl, benzyl, —$NH_2$, —NH($C_{1-4}$alkyl), —N($C_{1-4}$alkyl)$_2$, —$NO_2$, —S($C_{1-4}$alkyl), —$SO_2$($C_{1-4}$alkyl), —$CO_2$($C_{1-4}$alkyl), and —O($C_{1-4}$alkyl).

The term "alkoxy" means a group having the structure —OR', where R' is an optionally substituted alkyl or cycloalkyl group. The term "heteroalkoxy" similarly means a group having the structure —OR, where R is a heteroalkyl or heterocyclyl.

The term "amino" means a group having the structure —NR'R", where R' and R" are independently hydrogen or an optionally substituted alkyl, heteroalkyl, cycloalkyl, or heterocyclyl group. The term "amino" includes primary, secondary, and tertiary amines.

The term "oxo" as used herein means an oxygen that is double bonded to a carbon atom.

The term "alkylsulfonyl" as used herein means a moiety having the formula —S($O_2$)—R', where R' is an alkyl group. R' may have a specified number of carbons (e.g. "$C_{1-4}$ alkylsulfonyl")

The term "pharmaceutically acceptable salts," as used herein, refers to salts of compounds of this invention that are substantially non-toxic to living organisms. Typical pharmaceutically acceptable salts include those salts prepared by reaction of a compound of this invention with an inorganic or organic acid, or an organic base, depending on the substituents present on the compounds of the invention.

Non-limiting examples of inorganic acids which may be used to prepare pharmaceutically acceptable salts include: hydrochloric acid, phosphoric acid, sulfuric acid, hydrobromic acid, hydroiodic acid, phosphorous acid and the like. Examples of organic acids which may be used to prepare pharmaceutically acceptable salts include: aliphatic mono- and dicarboxylic acids, such as oxalic acid, carbonic acid, citric acid, succinic acid, phenyl-heteroatom-substituted alkanoic acids, aliphatic and aromatic sulfuric acids and the like. Pharmaceutically acceptable salts prepared from inorganic or organic acids thus include hydrochloride, hydrobromide, nitrate, sulfate, pyrosulfate, bisulfate, sulfite, bisulfate, phosphate, monohydrogenphosphate, dihydrogenphosphate, metaphosphate, pyrophosphate, hydroiodide, hydro fluoride, acetate, propionate, formate, oxalate, citrate, lactate, p-toluenesulfonate, methanesulfonate, maleate, and the like.

Suitable pharmaceutically acceptable salts may also be formed by reacting the agents of the invention with an organic base such as methylamine, ethylamine, ethanolamine, lysine, ornithine and the like. Pharmaceutically acceptable salts include the salts formed between carboxylate or sulfonate groups found on some of the compounds of this invention and inorganic cations, such as sodium, potassium, ammonium, or calcium, or such organic cations as isopropylammonium, trimethylammonium, tetramethylammonium, and imidazolium.

It should be recognized that the particular anion or cation forming a part of any salt of this invention is not critical, so long as the salt, as a whole, is pharmacologically acceptable.

Additional examples of pharmaceutically acceptable salts and their methods of preparation and use are presented in Handbook of Pharmaceutical Salts: Properties, Selection and Use (2002), which is incorporated herein by reference.

An "isomer" of a first compound is a separate compound in which each molecule contains the same constituent atoms as the first compound, but where the configuration of those atoms in three dimensions differs. Unless otherwise specified, the compounds described herein are meant to encompass their isomers as well. A "stereoisomer" is an isomer in which the same atoms are bonded to the same other atoms, but where the configuration of those atoms in three dimensions differs. "Enantiomers" are stereoisomers that are mirror images of each other, like left and right hands. "Diastereomers" are stereoisomers that are not enantiomers.

II. Combination Therapy

The modified glucocorticoid in combination with ursolic acid and resveratrol leads to a synergistic effect on chronic inflammation and cancer development, by reducing inflammation induced by carcinogens, viruses, and bacteria. The combination of the modified glucocorticoid in addition to the ursolic acid and resveratrol attenuates gluconeogenesis.

Certain embodiments are directed to treating chronic inflammation and cancer with a modified glucocorticoid as described herein or a combination of a modified glucocorticoid as described herein, ursolic acid, and resveratrol.

Ursolic acid inhibits chronic inflammation. In diabetic rats, dietary ursolic acid decreases resting glucose levels, and improves glucose tolerance and insulin sensitivity.

Resveratrol is a phytonutrient found in the skin of red grapes and in other fruits. Like ursolic acid, it also exerts many of its beneficial effects through its ability to mimic calorie restriction and exercise.

A. Skin Cancer

There are over one million new cases of skin cancer diagnosed in the United States each year (Rogers et al. *Arch. Dermatol.* 2010, 146(3):283-287). In addition, skin cancer is associated with a 15-30% increased risk of other forms of cancer (Kahn et al. *JAMA*. 1998 280(10):910-912; Krueger et al. *Can. J. Public Health.* 2010, 101(4):123-27). This indicates the importance of mechanisms to prevent or treat skin cancer. Skin cancer consists primarily of melanoma, basal cell carcinoma, and squamous cell carcinoma. Skin cancers have higher risk with increased UV exposure (Boscoe and Schymura. *BMC Cancer.* 2006 6:264; Lea et al. *Ann. Epidemiol.* 2007, 17(6):447-453) and higher prevalence in individuals with inflammatory disorders (Frentz and Olsen. *Br. J. Dermatol.* 1999, 140(2):237-242; Long et al. *Clin. Gastroenterol. Hepatol.* 2010, 8(3):268-274).

Cancer develops via three phases: initiation, promotion, and progression. During initiation, DNA mutations lead to activation of oncogenes and inactivation of tumor suppressor genes. DNA mutations in skin cancer are caused by environmental insults such as UV exposure and polycyclic aromatic hydrocarbons (PAHs). PAHs are present in smoke and can form DNA adducts when metabolized (Baird et al *Eniron. Mol. Mutagen.* 2005, 45(2-3):106-144; Boffetta et al, *Cancer Causes Control.* 1997 8(3):444-472). In tumor promotion, activated oncogenes and inactivated tumor suppressor genes cause constitutive activation of tumor-promoting signal transduction pathways. These pathways increase factors for cell proliferation, cell growth, resistance to apoptosis, and angiogenesis (Walaszek et al. *Chest.* 2004, 125(5 Suppl):128S-133S). Finally, tumor progression occurs when additional genetic alterations allow tumor cells to enter the bloodstream and metastasize to distant organ sites (Gialeli et al. *FEBSJ* 2011, 278(1):16-27).

The tumor promotion phase is characterized by abnormal activity of many signal transduction pathways, including the nuclear factor kappa B (NFKB) pathway. NFKB is a transcription factor that typically exists as heterodimer of p65 and p50 subunits. A number of tumor-promoting factors including UV light (Kato et al. *Mol Cell* 2003, 12(4):829-839; Lee et al. *Int J Mol Med* 2009, 23(5):679-684) and various tobacco constituents (Raj endrasozhan et al. *Pulm Pharmacol Ther* 2010, 23(3):172-181; Tsurutani et al. *Carcinogenesis* 2005, 26(7):1182-1195) activate the NFKB pathway. These stimuli phosphorylate and activate kinases that phosphorylate the NFKB inhibitor 1 KBa, targeting it for degradation by proteaseomes. Stimuli including UV light (Laszlo and Wu. *Photochem Photobiol* 2008, 84(6):1564-1568), smoke (Rajendrasozhan et al. *Pulm Pharmacol Ther* 2010, 23(3):172-181), or inflammatory agents (Hsing et al. *PLoS One* 2011, 6(3):e17598) also phosphorylate the active p65 subunit of NFKB at serines 536 and/or 276, allowing it to recruit histone acetyltransferases (HATs) (Chen et al. *Mol Cell Biol* 2005, 25(18):7966-7975). These HATs acetylate p65 at a number of lysine residues, resulting in dissociation of NFKB from its inhibitor IKBa (Chen et al. *EMBO J* 2002, 21(23):6539-6548; Kiernan et al. *J Biol Chem* 2003, 278 (4):2758-2766). Once free from IKBa, NFKB can translocate to the nucleus where it transcribes factors for cell proliferation, inflammation, resistance to apoptosis, angiogenesis, and metastasis (Kundu and Surh. *Mutat Res* 2008, 659(1-2):15-30).

Certain phytochemicals present in fruits and vegetables can inhibit cancer formation and growth in many experimental models. Also, epidemiological studies show that consumption of phytochemical-rich fruits and vegetables decreases the risk of many cancer types including skin cancer (Ibiebele et al. *Am J Clin Nutr* 2007, 85(5):1401-1408; Kune et al. *Nutr Cancer* 1992, 18(3):237-244). Resveratrol inhibits formation of many tumor types in animal models, including those of the skin (Aziz et al. *FASEB J* 2005, 19(9):1193-1195; Kapadia et al. *Pharmacol Res* 2002, 45(6):499-505). Ursolic acid (UA) also inhibits tumor formation in a number of models including chemically-induced skin cancer (Huang et al. *Cancer Res* 1994, 54(3):701-708; Tokuda et al. *Cancer Lett* 1986, 33(3):279-285). Resveratrol and UA also inhibit NFKB signaling.

In addition to their anti-cancer effects, a wide range of phytochemicals and plant extracts have also been shown to inhibit the metabolic syndrome, including insulin resistance and diabetes (Xia and Weng. *J Diabetes* 2010, 2(4):243-249; Graf et al. *Curr Opin Investig Drugs* 2010, 11(10):1107-1115; Cherniack. *Nutrition* 2011, 27(6):617-623; Leiherer et al. *Vascul Pharmacol* 2013, 58(1-2):3-20). In many cases these effects are associated with AMP-activated kinase (AMPK), which also mediates the activities of prescribed anti-diabetic drugs like metformin (Hattori et al. *Hypertension* 2006, 47(6):1183-1188; Musi et al. *Diabetes* 2002, 51(7):2074-2081; Zhou et al. *J Clin Invest* 2001, 108(8): 1167-1174; Hardie et al. *Chem Biol* 2012, 19(10):1222-1236). AMPK is activated by exercise in humans and animals as indicated by an increase in phosphorylation of threonine 172 (Birk and Wojtaszewski. *J Physiol* 2006, 577(Pt 3):1021-1032; Hoene et al. *J Physiol* 2009, 587(Pt 1):241-252; Koopman et al. *Am J Physiol Endocrinol Metab* 2006, 290(6):E1245-1252). AMPK also plays a key role in NFKB inhibition by different compounds used to treat diabetes (Hattori et al. *Hypertension* 2006, 47(6):1183-1188; Tomizawa et al. *Metabolism* 2011,60(4):513-522).

Resveratrol and UA improve symptoms of metabolic syndromes and diabetic symptoms in both animal and humans (Baur et al. *Nature* 2006, 444(7117):337-342; Brasnyo et al. *Br J Nutr* 2011, 106(3):383-389; Jang et al. *Int Immunopharmacol* 2009, 9(1):113-119; Somova et al. *Phytomedicine* 2003, 10(2-3):115-121). Resveratrol activates AMPK in many organisms including humans (Timmers et al. *Cell Metab* 2011, 14(5):612-622; Xu and Si. *Nutr Res* 2012,32(9):648-658), and the full effects of resveratrol on the metabolic syndrome depend on AMPK activity (Um et al. *Diabetes* 2010, 59(3):554-563). The cytotoxic effects of UA in different cancer cell lines are also dependent on AMPK activation (Son et al. *Phytother Res* 2013; Zheng et al. *Biochem Biophys Res Commun* 2012, 419(4):741-747). Finally, AMPK activity suppresses tumorigenesis in tumor-susceptible animals (Huang et al. *Biochem J* 2008, 412(2):211-221; Faubert et al. *Cell Metab* 2013, 17(1):113-124). These results indicate the anti-cancer and anti-diabetic effects of many natural compounds like resveratrol and UA may be mediated by AMPK activation.

There are many potential synergistic mechanisms for different phytochemical combinations. One drug may modulate the metabolism of the other (Kimura et al. *Food Chem Toxicol* 2010, 48(1):429-435; Taesotikul et al. *Drug Metab Pharmacokinet* 2011, 26(2):154-161), or impact its ability to enter the bloodstream (Lu et al. *J Nutr Biochem* 2005, 16(1):23-30) or the cell (Suganuma et al. *Cancer Res* 1999, 59(1):44-47). Drugs can also enhance the ability of each other to induce similar downstream effects, many times by acting along different points on cell regulatory systems (Khafif et al. *Carcinogenesis* 1998, 19(3):419-424; Saw et al. *Biopharm Drug Dispos* 2011, 32(5):289-300).

Resveratrol has been shown to synergistically inhibit tumor cell growth through different mechanisms. Resveratrol has been shown to potentiate the cytotoxic effect of doxorubicin and docetaxel in MCF-7 breast cancer cells, and to enhance doxorubicin concentration in other cancer cell lines (Al-Abd et al. *Cell Prolif* 2011;44(6):591-601). Resveratrol has also been shown to enhance cytotoxic effects of vincristine, paclitaxel, and doxorubicin in drug-resistant human epidermoid carcinoma line KBv200. Resveratrol has also been shown to decrease the expression of anti-apoptotic bcl-2 and drug efflux pump p-glycoprotein in these chemoresistant cells (Quan et al. *Biomed Pharmacother* 2008;62(9):622-629).

Ursolic acid has been shown to decrease viability of a number of chemoresistant cancer cell types, however the IC50 for UA was still lower in the parental cells (Shan et al. *Chin J Integr Med* 2011, 17(8):607-611), which have lower levels of p-glycoprotein (Zhang et al. *Int J Biochem Cell Biol* 2012, 44(8):1244-1253; Shi et al. *Eur J Pharmacol* 2011;669(1-3):38-44). These results described herein show the effects of UA can be enhanced by compounds such as resveratrol, which subvert traditional resistance phenotypes. The effects of UA and resveratrol were tested in various skin-relevant systems, including in vivo mouse skin, human keratinocytes, and skin cancer cell lines to determine if this combination has a synergistic effect.

III. Formulation and Administration

Modified glucocorticois described herein, ursolic acid, and/or resveratrol can be administered to a subject either orally, parenterally (e.g., intravenously, intramuscularly, or subcutaneously), intraperitoneally, or locally (for example, powders, ointments or drops). In certain aspects the compounds are provided in a nutritional supplement formulation or a therapeutic formulation.

A nutritional supplement formulation can be in any form, e.g., liquid, solid, gel, emulsion, powder, tablet, capsule, or gel cap (e.g., soft or hard gel cap). A nutritional supplement formulation typically will include one or more compositions that have been purified, isolated, or extracted (e.g., from plants) or synthesized, which are combined to provide a benefit (e.g., a health benefit in addition to a nutritional benefit) when used to supplement food in a diet.

Compositions suitable for parenteral injection may comprise physiologically acceptable sterile aqueous or nonaqueous solutions, dispersions, suspensions, or emulsions, or may comprise sterile powders for reconstitution into sterile injectable solutions or dispersions. Examples of suitable aqueous and nonaqueous carriers, diluents, solvents, or vehicles include water, ethanol, polyols (propylene glycol, polyethylene glycol, glycerol, and the like), suitable mixtures thereof, triglycerides, including vegetable oils such as olive oil, or injectable organic esters such as ethyl oleate. Proper fluidity can be maintained, for example, by the use of a coating such as lecithin, by the maintenance of the required particle size in the case of dispersions, and/or by the use of surfactants.

These compositions may also contain adjuvants such as preserving, wetting, emulsifying, and/or dispersing agents. Prevention of microorganism contamination of the compositions can be accomplished by the addition of various antibacterial and antifungal agents, for example, parabens, chlorobutanol, phenol, sorbic acid, and the like. It may also be desirable to include isotonic agents, for example, sugars, sodium chloride, and the like. Prolonged absorption of injectable pharmaceutical compositions can be brought about by the use of agents capable of delaying absorption, for example, aluminum monostearate and/or gelatin.

Solid dosage forms for oral administration include capsules, tablets, powders, and granules. In such solid dosage forms, the active compound is admixed with at least one inert customary excipient (or carrier) such as sodium citrate or dicalcium phosphate or (a) fillers or extenders, as for example, starches, lactose, sucrose, mannitol, or silicic acid; (b) binders, as for example, carboxymethylcellulose, alginates, gelatin, polyvinylpyrrolidone, sucrose, or acacia; (c) humectants, as for example, glycerol; (d) disintegrating agents, as for example, agar-agar, calcium carbonate, potato or tapioca starch, alginic acid, certain complex silicates, or sodium carbonate; (e) solution retarders, as for example, paraffin; (f) absorption accelerators, as for example, quaternary ammonium compounds; (g) wetting agents, as for example, cetyl alcohol or glycerol monostearate; (h) adsorbents, as for example, kaolin or bentonite; and/or (i) lubricants, as for example, talc, calcium stearate, magnesium stearate, solid polyethylene glycols, sodium lauryl sulfate, or mixtures thereof. In the case of capsules and tablets, the dosage forms may also comprise buffering agents.

Solid compositions of a similar type may also be used as fillers in soft or hard filled gelatin capsules using such excipients as lactose or milk sugar, as well as high molecular weight polyethylene glycols, and the like.

Solid dosage forms such as tablets, capsules, and granules can be prepared with coatings or shells, such as enteric coatings and others well known in the art. They may also contain opacifying agents, and can also be of such composition that they release the active compound or compounds in a delayed manner. Examples of embedding compositions that can be used are polymeric substances and waxes. The active compounds can also be in micro-encapsulated form, if appropriate, with one or more of the above-mentioned excipients.

Liquid dosage forms for oral administration include acceptable emulsions, solutions, suspensions, syrups, and elixirs. In addition to the active compounds, the liquid dosage form may contain inert diluents commonly used in the art, such as water or other solvents, solubilizing agents and emulsifiers, as for example, ethyl alcohol, isopropyl alcohol, ethyl carbonate, ethyl acetate, benzyl alcohol, benzyl benzoate, propylene glycol, 1,3-butylene glycol, dimethylformamide, oils, in particular, cottonseed oil, groundnut oil, corn germ oil, olive oil, castor oil, sesame seed oil, glycerol, tetrahydrofurfuryl alcohol, polyethylene glycols, fatty acid esters of sorbitan, or mixtures of these substances, and the like.

Suspensions, in addition to the active compound(s), may contain suspending agents, as for example, ethoxylated isostearyl alcohols, polyoxyethylene sorbitol or sorbitan esters, microcrystalline cellulose, aluminum metahydroxide, bentonite, agar-agar, or tragacanth, or mixtures of these substances, and the like.

Dosage forms for topical administration of modified glucocorticoid as described herein, ursolic acid, and/or resveratrol include ointments, powders, sprays and inhalants. The compound(s) are admixed with a physiologically acceptable carrier, and any preservatives, buffers, and/or propellants that may be required.

For the compounds of the present invention, alone or as part of a supplement composition, the doses are between about 1, 100, 200, 300, 400, 500, 600 to 500, 600, 700, 800, 900, 1000 mg, preferably between 200 and 600 mg. In certain aspects, the ratio of ursolic acid to resveratrol can vary between about 4:1, 3:1 2:1, 1:1, 1:2, 1:3 to 1:4. In certain aspects, the compounds are administered 1, 2, 3, 4, 5, 6, 7, 8, 9, or 10 times per day. In certain aspects, the compounds are administered once every 1, 2, 3, 4, 5, 6, or 7 days.

The term "effective amount" means an amount effective, at dosages and for periods of time necessary, to achieve the desired therapeutic or prophylactic result.

An "effective amount" in reference to decreasing cancer cell growth, means an amount capable of decreasing, to some extent, the growth of some cancer or tumor cells. The term includes an amount capable of invoking a growth inhibitory, cytostatic and/or cytotoxic effect and/or apoptosis of the cancer or tumor cells. Effective doses will be easily determined by one of skill in the art and will depend on the severity and course of the disease, the patient's health and response to treatment, the patient's age, weight, height, sex, previous medical history and the judgment of the treating physician.

The term "subject" means animals, such as dogs, cats, cows, horses, sheep, geese, and humans. Particularly preferred patients are mammals, including humans of both sexes.

The terms "treating", "treat" and/or "treatment" include preventative (e.g., prophylactic) and palliative treatment.

IV. Examples

The following examples as well as the figures are included to demonstrate preferred embodiments of the invention. It should be appreciated by those of skill in the art that the techniques disclosed in the examples or figures represent techniques discovered by the inventors to function well in the practice of the invention, and thus can be considered to constitute preferred modes for its practice. However, those of skill in the art should, in light of the present disclosure, appreciate that many changes can be made in the specific embodiments which are disclosed and still obtain a like or similar result without departing from the spirit and scope of the invention.

Using an in vitro model a significant amount of up-regulation of 11βHSD2 protein expression was identified in non-melanoma skin cancer cells versus normal counter parts. This observation lead to two modifications to the glucocorticoid structure (see FIG. 1). First, the hydroxyl group was removed at the eleventh carbon position to circumvent the upregulation of 11βHSD2 and was replaced with a halogen. Second, two hydrogens were added to saturate the double bond between carbons four and five, a 5-α-reduction, which is the location of cortisol that induces gluconeogenesis. Similar modifications can be done in dexamethasone, triamcinolone, and fluocinolone acetonide.

Figure 2:
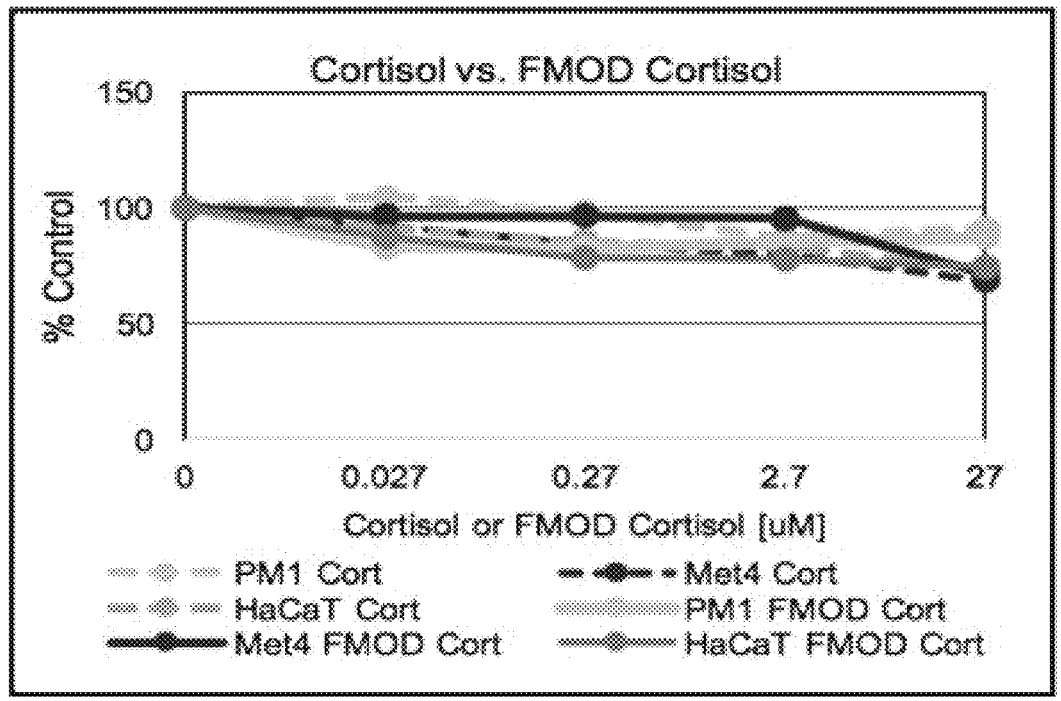
FIG. 2. MTT assay for cell viability.

MTT assay displayed in FIG. 2 was used to measure viability of each cell line when treated with a range of cortisol and 11-deoxyfluorocortisol (F-MOD) concentrations. When comparing the effect of F-MOD and cortisol on cell proliferation, normal HaCaT cells were found to be more sensitive to glucocorticoid treatment compared to cancerous PM1 and Met4 cells. The potency of F-MOD against cell proliferation is at least as powerful as the original cortisol if not stronger as seen in PM-1.

Figure 3:
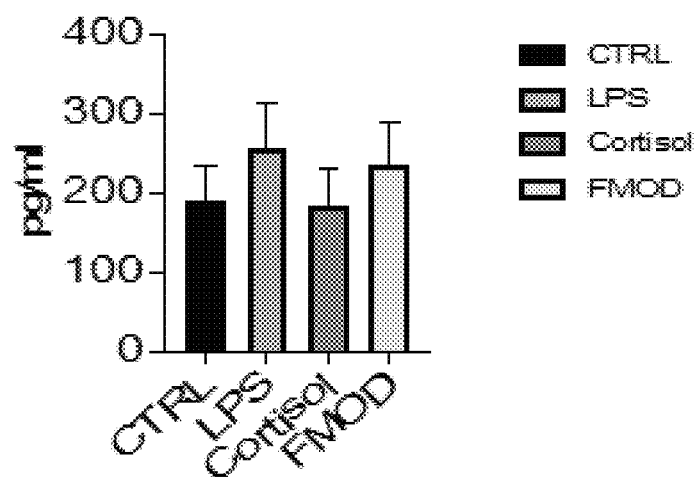
FIG. 3. IL-6 ELISA.
Figure 4:
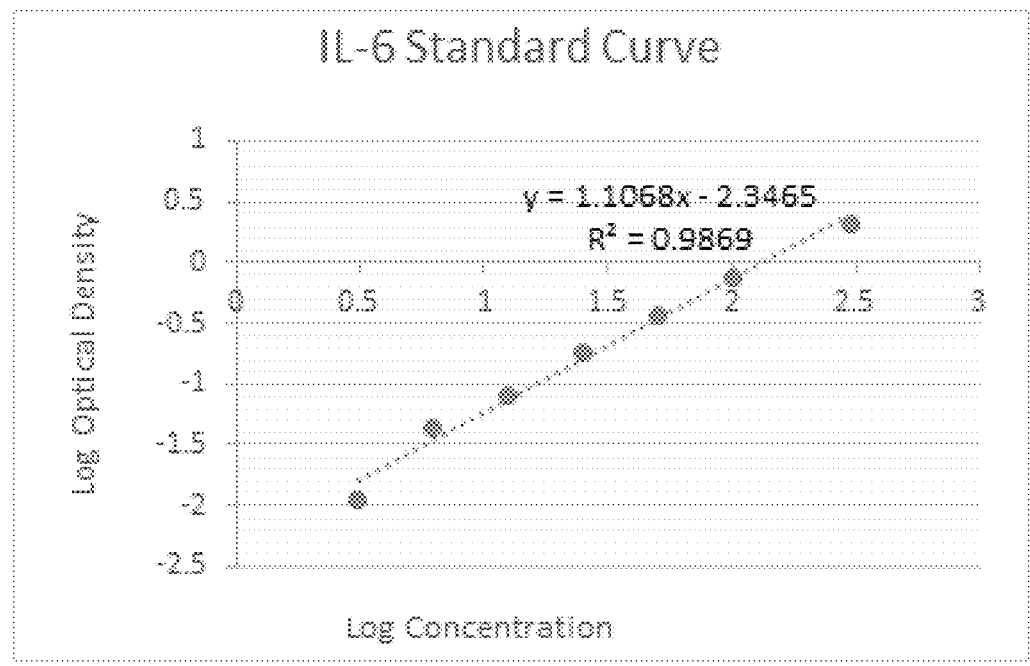
FIG. 4. Concentrations of IL-6 detected in HaCaT cells. CTRL: no glucocorticoid treatment, no LPS. LPS: no glucocorticoid treatment, +LPS Cortisol: treatment with cortisol, +LPS F-MOD: treatment with 11-deoxyfluorocortisol, +LPS FIG. 5. qPCR analysis of LPS-induced IL-1β mRNA.
Figure 5:
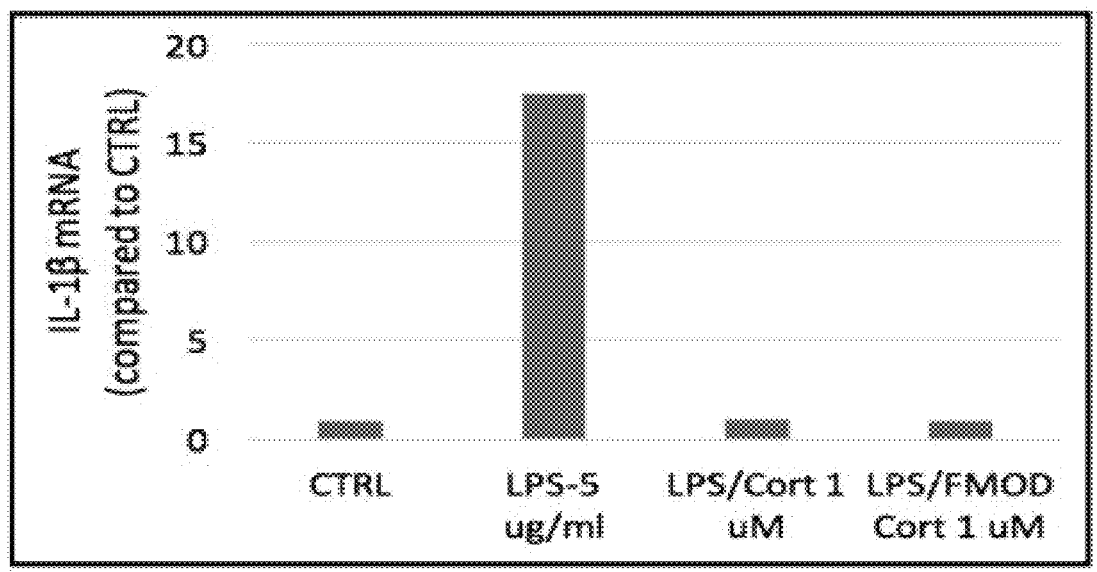

Enzyme-linked immunosorbent assays (ELISAs) analysis was performed (FIG. 3) to identify the ideal concentrations of modified glucocorticoids which display the most delayed or prevented inflammation through biomarker, IL-6. The inventors tested three human skin cell lines: HaCaT, PM-1, and Met 4, using LPS to mimic the inflammatory response. An increase of IL-6 was observed in the HaCaT cells. FIG. 4 shows the concentrations of IL-6 in the HaCaT cells with error bars and its corresponding standard curve.

qPCR analysis is shown FIG. 5. LPS-induced inflammation in HaCat cells showed that the LPS-induced increase of inflammatory cytokine IL-1β was significantly suppressed to a similar extent by cortisol and F-MOD.

The modified cortisol in combination with ursolic acid and resveratrol lead to a synergistic effect on inflammation and cancer development. The combination of the modified cortisol in addition to the ursolic acid and resveratrol will have less side effects than the modified cortisol alone.

The invention claimed is:
1. A modified glucocorticoid compound of the following structure:

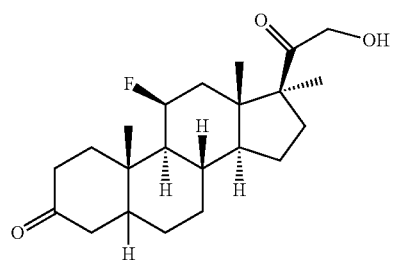

or a pharmaceutically acceptable salt thereof.

2. A pharmaceutical composition comprising the compound of claim 1.

\* \* \* \* \*